US005834465A

United States Patent [19]
Olney

[11] Patent Number: 5,834,465
[45] Date of Patent: Nov. 10, 1998

[54] TREATMENT WITH COMBINED NMDA AND NON-NMDA ANTAGONISTS TO REDUCE EXCITOTOXIC CNS DAMAGE

[75] Inventor: John W. Olney, St. Louis, Mo.

[73] Assignee: Washington University, St. Louis, Mo.

[21] Appl. No.: 877,839

[22] Filed: May 1, 1992

Related U.S. Application Data

[63] Continuation-in-part of Ser. No. 467,139, Jan. 18, 1990, abandoned, which is a continuation-in-part of Ser. No. 424,548, Oct. 20, 1989, Pat. No. 5,034,400.

[51] Int. Cl.$^6$ .................. A61K 31/54; A61K 31/515; A61K 31/44; A61K 31/445
[52] U.S. Cl. .................. 514/226.2; 514/270; 514/289; 514/315; 514/318
[58] Field of Search .................. 514/226.2, 270, 514/289, 315, 318

[56] References Cited

U.S. PATENT DOCUMENTS

| | | | |
|---|---|---|---|
| 4,806,543 | 2/1989 | Choi | 514/464 |
| 4,833,148 | 5/1989 | Olney | 514/270 |
| 4,888,347 | 12/1989 | Woodruff et al. | 514/289 |

OTHER PUBLICATIONS

Boast, C.A., *Neurology and Neurobiology 46:* 691–698 (1988).
Honore, T., et al, *Science 241:* 701–703 (1988).
Drejer, J. and Honore, T., *Neurosci. Letters 87:* 104–108 (1988).
Price, M.T., et al, *Society of Neuroscience Abstracts 14:* 418 (abstract #168.9; Nov. 1988).
Olney, J.W., et al, *J. Neurosci. 9:* 1701 (1989).
Honore, T., et al, *J. Neurochem. 52 (Suppl.)*: abstract S42–A (1989).
Sheardown, M.J., et al, *Science 247:* 571–574 (1990).
I. Tarnawa et al, pp. 538–546 in Labee and Rosenthal, eds., *Amino Acids: Chemistry, Biology and Medicine* (1990).
Zeevalk, G.D. and Nicklas, W.J., *J Pharmacol Exp Ther 253(3):* 1285–1292 (1990).
Rothman, S.M., et al, in *Glutamate, Cell Death and Memory* (P Ascher et al, eds., Springer–Verlag, Berlin Heidelberg, 1991).
Goldberg, M.P., et al, *J Pharmacol Exp Ther 243(2):* 784–791 (1987).
Goldberg, M.P., et al, *J Pharmacol Exp Ther 245 (2):* 1081–1086 (1988).
Choi, D.W., et al, *J Pharmacol Exp Ther 242(2):* 713–720 (1987).
Monyer, H., et al, *Brain Res 483:* 347–354 (1989).
Buchan, A. and Pulsinelli, W.A., *J. Neuroscience 10:* 311–316 (1990).
Buchan, A.M., et al, *Neurosci. Letters 132:* 255–258 (1991).
Sheardown, M.J., et al, pp. 245–253 in Krieglstein, J., and Oberpichler, H., eds., *Pharmacology of Cerebral Ischemia 1990* (Wissenschaftliche Verlagsgesellschaft, Stuttgart, Germany, 1990).
Michenfelder, J., et al, *Brain Research 481:* 228–234 (1989).
Lanier, W., et al, *Anesthes. Rev. 15:* 36–37 (1988).
Nellgard, B. and Wieloch, T., *J Cereb Blood Flow Metab 12:* 2–11 (1992).
Nellgard, B., et al, *Anesthesiology 75:* 279–287 (1991).
Olney, J.W., et al, *Science 244:* 1360–1362 (1989).
Mosinger, J.L. & Olney, J.W., *Society of Neuroscience Abstracts 15:* 45 (abstract #23.22; Oct. 1989).
Mosinger, J.L. and Olney, J.W., *Exper. Neurol. 105:* 110–113 (1989).
Salt, T.E. and Eaton, S.A., *Exper. Brain Research 77 (3):* 646–652 (1989).
Boast, *Neurology and Neurobiology 46:* 691–698 (1988).
Honore et al., *Science 241:* 701–703 (1988).
Drejer et al., *Neurosci. Letters 87:* 104–108 (1988).
Price et al., *Society of Neuroscience Abstracts 14:* 418 (ab #168.9) 1988.
Olney et al. *Eur. J. Pharmacol. 142:* 319–320 (1987).

*Primary Examiner*—Kevin E. Weddington
*Attorney, Agent, or Firm*—Patrick D. Kelly

[57] ABSTRACT

This invention involves a pharmaceutical mixture for preventing or reducing excitotoxic brain damage caused by hypoxia/ischemia (such as stroke) and various other factors. This mixture comprises an NMDA antagonist and a non-NMDA antagonist, both of which penetrate blood-brain barriers (BBB's) and which, in combination, provide greater protection against excitotoxic damage than can be provided by any quantity of either agent by itself. Suitable NMDA antagonists can be either competitive antagonists which bind directy to the NMDA binding site in the NMDA receptor complex, or non-competitive agents that interact with other binding sites such as the PCP, glycine, or polyamine binding sites. Suitable non-NMDA antagonists include a quinoxalinedione compound referred to as NBQX, and a 2,3-benzodiazepine compound referred to as GYKI 52466. If an NMDA antagonist is used which is stronger than dextromethorphan, the mixture of an NMDA and a non-NMDA antagonist preferably should be administered in combination with a third agent that functions as a "safening agent" to prevent or reduce the neurotoxic side effects caused by strong NMDA antagonists. Two classes of safening agents have been identified: (1) anti-cholinergic agents such as scopolamine and, (2) barbiturates which act as direct agonists of gamma-amino-butyric acid (GABA) receptors, such as secobarbital, pentobarbital, and thiamylal.

17 Claims, No Drawings

TREATMENT WITH COMBINED NMDA AND NON-NMDA ANTAGONISTS TO REDUCE EXCITOTOXIC CNS DAMAGE

RELATED APPLICATIONS

This application is a continuation-in-part of U.S. application Ser. No. 467,139, filed on Jan. 18, 1990, now abandoned, which was a continuation-in-part of U.S. application Ser. No. 424,548, filed on Oct. 20, 1989, which issued as U.S. Pat. No. 5,034,400.

BACKGROUND OF THE INVENTION

This invention pertains to neurology and neuropharmacology. It describes methods and compounds which are safer and more effective than others currently available for protecting the brain against acute damage in conditions such as stroke, epilepsy, and physical trauma.

The most important excitatory neurotransmitters in the nervous systems of humans and other mammals are glutamate and aspartate. These are the ionized forms of glutamic acid and aspartic acid, and they have related structures as follows:

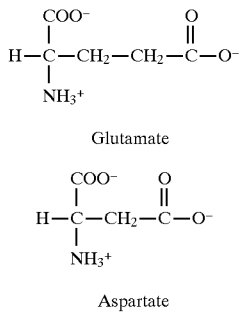

Since glutamic and aspartic acid are amino acids, this neurotransmitter system is called the excitatory amino acid (EAA) system. In order to transmit a nerve signal or impulse from one neuron to another, a neuron releases glutamate or aspartate into the fluid which fills the synaptic gap between the transmitting neuron and the receiving neuron. A molecule of glutamate or aspartate reacts with a receptor on the surface of the receiving cell, thereby causing the opening of an ion channel which allows calcium and sodium ions to enter the cell. The flow of ions into the cell provokes several reactions; typically, the excited neuron transmits the nerve impulse to other neurons, by releasing glutamate at some or all its own synapses.

A molecule of glutamate or aspartate does not bond to an EAA receptor; instead, it immediately disengages from the receptor and returns to the fluid in the synaptic gap between the transmitting neuron and the receiving neuron.

In the brain of a healthy mammal, glutamate and aspartate molecules which have already reacted with receptors are removed very rapidly from the synaptic fluid, by means of a transport mechanism (which can also be referred to as an uptake system, since the glutamate is taken up by the neurons). This transport/uptake system involves an active pumping mechanism which carries glutamate or aspartate back inside a neuron.

Under normal conditions, this transport mechanism prevents glutamate and aspartate from accumulating in the synaptic fluid. However, under certain conditions described below, the transport/uptake system cannot work properly. When this occurs, the same glutamate and aspartate molecules which normally function as neurotransmitters turn into lethal toxins that damage and destroy CNS neurons, in a process known as "excitotoxicity."

Relatively high concentrations of glutamate and aspartate are synthesized inside neurons in the CNS, but they are not allowed to accumulate in the extracellular fluid inside the brain or spinal cord, since they would provoke uncontrolled nerve impulses if they could contact EAA receptors on a random basis. It should also be noted that glutamate and aspartate cannot pass through the mammalian blood-brain barrier (BBB). Therefore, even though glutamate and aspartate normally circulate in the blood as a product of protein digestion, cellular synthesis, and ingestion of foods which contain ingredients such as monosodium glutamate as an additive, the glutamate and aspartate molecules in the blood cannot reach the EAA receptors on the surfaces of neurons in most regions of the brain. There is an exception to this rule, involving certain portions of the brain called circumventricular organs, which are not protected by the BBB and which therefore are at risk of excitatory damage, particularly in infants; however, those regions are not of direct interest to this particular invention and will not be discussed further.

Since glutamate is more prevalent than aspartate as an EAA neurotransmitter, the discussion below will focus on glutamate. However, it should be recognized that the following comments also apply to aspartate, which exerts the same activity as glutamate at EAA receptors.

Excitotoxicity

As mentioned above, an active glutamate transport system is used by healthy neurons to remove glutamate from extracellular fluid in the CNS. However, energy is required to drive that transport system, and under various conditions, neurons can lack the energy required to drive the system. Neurons in the CNS rely exclusively on oxygen and glucose for energy to drive the transport system as well as their other metabolic processes, and when inadequate supplies of either oxygen or glucose are present in the blood circulating through the brain, the transport system which clears glutamate out of the synaptic fluid cannot function properly and glutamate begins to accumulate in synaptic fluid. This condition can be caused by ischemia (i.e., a lack of adequate blood flow, as occurs in the brain during a stroke or cardiac arrest), hypoxia (inadequate oxygen supply, which occurs during ischemia and in certain other conditions such as carbon monoxide poisoning, drowning, suffocation, and perinatal asphyxia), and hypoglycemia (an inadequate supply of glucose in the blood, which can occur due to an overdose of insulin).

If the transport system cannot work properly and glutamate or aspartate begin to accumulate in the synapses, they cause repeated activation of the EAA receptors on the neurons; this causes the affected neurons to reach a severely over-excited condition. If this process reaches a level where neurons begin to die from over-excitation, it is referred to as "excitotoxicity."

In a situation which initially involves only localized ischemia/hypoxia (such as a localized stroke caused by blockage of one particular artery), excitotoxic damage can spread beyond the region that is initially affected, due to several processes. The initially affected neurons are being given repeated excitatory signals at their EAA receptors; they interpret those signals as commands to release their own glutamate at additional synapses, and that type of secondary glutamate release can stimulate additional neurons. This process can take on an uncontrolled, runaway condition, and it is further aggravated by the fact that overexcited neurons consume even more oxygen as they try to cope with the increased metabolic demands being placed on them; this further depletes any oxygen or glucose in any nearby blood or other fluids, which makes the situation more critical.

To make matters even worse, neuron damage cannot be reversed or even halted merely by restoring blood flow to the affected region of the brain. Instead, damage and cell death often increases sharply when oxygen is reintroduced after a period of hypoxia. During hypoxia, an enzyme called xanthine dehydrogenase is converted into a different form known as xanthine oxidase, which converts oxygen molecules ($O_2$) into highly reactive ion radicals known as superoxide. Superoxide randomly attacks and destroys molecules and cells; it also promotes the release of iron ions from ferritin, which in turn promotes a process called "lipid peroxidation" which destroys cell membranes.

If large numbers of neurons are killed by an excitotoxic event such as a stroke or cardiac arrest, it can lead to the death of the patient or animal, or to irreversible brain damage. Under the current state of medical technology, neurons do not regenerate, and such brain damage is permanent and irreversible; although nerve growth factors are being actively studied, it will be many years before they can be used on humans. Therefore, a baby whose brain suffers just a few minutes of oxygen deprivation during birth is likely to be retarded or crippled by cerebral palsy for an entire lifetime. This type of brain damage is one of the most tragic injuries any child can suffer. The amount of suffering and heartbreak, and the costs of providing medical care and daily maintenance to children who suffered perinatal asphyxia, and to adults suffering paralysis, speech loss, memory loss, or other problems due to stroke or other forms of ischemia/hypoxia, are staggering.

An enormous amount of research is being done on drugs that might someday be able to reduce the brain damage caused by stroke and other forms of ischemia/hypoxia, and numerous review articles and entire books are entirely devoted to describing that research. Recent review articles include Krause et al 1988, Meyer et al 1987, and Wauguier et al 1987. An important series of books entitled *Pharmacology of Cerebral Ischemia* is issued each year, shortly after a major international conference devoted entirely to cerebral ischemia; see Krieglstein 1989, and Krieglstein and Oberpichler 1990. Also see Cavalheiro et al 1988 and Ascher et al 1991 for additional book-length discussions. Several scientific and medical journals are entirely or predominantly devoted to stroke and cerebrovascular problems, such as *Stroke, Journal of Cerebral Blood Flow and Metabolism,* and *Cerebrovascular Brain Metabolism Review*, while other journals such as *Brain Research, Journal of Neuroscience, Journal of Neurochemistry,* and *Neurology* also publish numerous articles which directly relate to neurological hypoxia and ischemia.

However, despite all the research that has been done by thousands of scientists and doctors working in this field, no effective treatments are currently available to reduce the brain damage cause by stroke or other excitotoxic conditions.

It should also be noted that excitotoxic processes are also involved in a number of processes that do not directly involve hypoxia or ischemia. For example, certain types of food poisoning and viral infections that attack the CNS are attributable to hyper-stimulation of EAA receptors. In addition, certain combinations of otherwise useful drugs, such as lithium and pilocarpine, can cause excitotoxic reactions if administered by physicians who are not aware of the presence of both drugs in a single patient. Also, certain types of epileptic seizures (including a type of on-going seizure known treatments as temporal lobe epilepsy or status epilepticus) involve over-excitation by certian regions of the brain in patterns that are believed to cause excitotoxic damage, and excitotoxicity is believed to be a component of the ongoing deterioration of some types of progressive neurodegenerative diseases. These and other disease conditions which appear to involve excitoxicity are discussed in more detail in U.S. Pat. No. 5,034,400.

NMDA Antagonists

In an effort to develop drugs for reducing excitotoxic brain damage, many researchers have studied drugs known as "NMDA antagonists," which suppress activity the NMDA subtype of glutamate receptor; these receptor types are discussed in more detail below.

In pharmacological terminology, an "agonist" is a molecule which binds to and activates a certain type of receptor. For example, glutamate molecules acting at EAA receptors, and insulin molecules acting at insulin receptors, are both agonists at their respective receptors. Other agonists can include drugs that do not normally exist inside the body; for example, NMDA functions as an agonist at NMDA receptors, while kainic acid functions as an agonist at KA receptors (another type of EAA receptor).

By contrast, an "antagonist" is a molecule which blocks or reduces the effects exerted by a natural molecule at a receptor. This can happen in any of several ways. A "competitive antagonist" binds to and occupies a certain binding site at a receptor, without triggering the normal activity at the receptor; this binding action prevents the natural messenger molecule from reaching and activating the receptor. Competitive antagonists which suppress activity at NMDA receptors by binding directly to the NMDA binding site include:

CGP 40116 (the common name for D-(E)-2-amino-4-methyl-5-phosphone-3-pentenoic acid); see Fagg et al 1989

CGP 37849 (the common name for 2-amino-4-methyl-5-phosphono-3-pentenoic acid); see Fagg et al 1989

CGS 19755 (the common name for cis-4-phosphonomethyl-2-piperidinecarboxylic acid); see Boast 1988

CGP 39551 (the common name for D,L(E)-2-amino-4-methyl-5-phosphono-3-pentenoic acid carboxyethyl ester)

D-CPP-ene (an enantiomer of (4-(3-phosphonoprop-2-enyl)-piperazine-2-carboxylic acid); see Lowe et al 1990 and McCulloch et al 1990

NPC 12626 (the common name for 2-amino-4,5-(1,2-cyclohexyl)-7-phosphonoheptanoic acid); see Borosky et al 1988

As mentioned above, all of the foregoing drugs are competitive antagonists which block NMDA activity by binding directly to the NMDA binding site in NMDA receptors. However, the NMDA receptor is a highly complex assembly which is believed to contain five distinct binding sites: the NMDA binding site, a glycine binding site, a polyamine binding site, a zinc binding site, and a PCP binding site. Each binding site reacts with a different type of ligand, and various drugs have been discovered which act as non-competitive antagonists by binding to sites other than the NMDA binding site. For example, 7-chlorokynurenic acid and MNQX appear to suppress glutamate activity at NMDA receptors by antagonizing the glycine binding site (Kemp et al 1988 and Drejer et al 1989), while ifenprodil (which is 4-benzyl-alpha-(p-hydroxyphenyl)-beta-methyl-1-piperidine-ethanol) and SL 82.0715 (which is (±)-2-(4-chlorophenyl)-4-[-(4-fluorophenyl)methyl]-1-piperadine ethanol) reportedly act at the polyamine binding site (Gotti et al 1988 and Carter et al 1989).

An important class of non-competitive NMDA antagonists are drugs which activate the phencyclidine (PCP) binding site in the NMDA complex. The most effective non-competitive NMDA antagonist ever discovered is a drug called MK-801; it is also called dizocilpine. The full chemical name is (+)-5-methyl-10,11-dihydro-5H-di[a,d]-cyclohepten-5,10-imine. It is usually formulated as the maleate salt. MK-801 is both powerful and highly selective at the PCP binding site; it has no other known binding activities, and it blocks the passage of ion currents through the NMDA ion channel, regardless of what is happening at any other binding site in the NMDA receptor complex (this activity is known as an open-channel block).

During the mid-to-late 1980's, MK-801 was hailed by numerous research teams as a highly effective drug which could reduce excitotoxic damage in a variety of in vitro tests (involving isolated neurons in tissue culture conditions) and even in several types of in vivo tests involving intact animals. Articles and patents from that period which claimed that MK-801 provided effective protection against various types of ischemia include the following:

(1) Wong et al 1986, Kemp et al 1987, U.S. patent (Woodruff et al), all of which describe the results of in vitro (cell culture) tests;

(2) Foster et al 1987, Gill et al 1987, and McDonald et al 1987, which describe the results of in vivo tests on rats and gerbils;

(3) Kochar et al 1988, which describe the results of in vivo tests on rabbits;

(4) Ozyurt et al 1988 and Park et al 1988, which describe the results of in vivo tests on cats.

Despite those optimistic early reports, subsequent tests involving larger animals and/or other models of stroke, hypoglycemia, and other excitotoxic damage cast severe doubt on the ability of MK-801 to prevent excitotoxic damage in large mammals or humans. Those reports are cited and discussed in more detail below. In addition, research by the Applicant revealed that MK-801 causes toxic side effects in which certain types of neurons in the cingulate/retrosplenial cortex are killed or severely damaged. This damage is manifested by vacuole formation, mitochondrial dissolution, and necrosis in the affected neurons, and in hallucinations and other psychotomimetic effects and the potentiation of certain types of seizures (Olney et al 1989). For these and possibly other reasons, MK-801 was abandoned in the early 1990's as a potential therapeutic drug.

Other drugs which function as NMDA antagonists due to activity at the PCP binding site include phencyclidine (PCP, which is widely abused under the street name "angel dust") and ketamine and tiletamine, which are sometimes used as anesthetics but which can cause reactions known as "emergence psychosis."

All of the NMDA antagonists listed above penetrate the mammalian blood-brain barrier (BBB) in sufficient quantities to affect neurons inside the CNS if injected subcutaneously or intravenously; some are also effective if ingested orally. Various other compounds such as D-AP5, D-AP7, and alpha amino adipate also act as NMDA antagonists in tissue culture, but they do not penetrate the BBB in sufficient quantity to function effectively in vivo.

Two other drugs, dextromethorphan and dextrorphan, also act as NMDA antagonists; they penetrate the BBB and are widely used in cough syrup, and they have been suggested as useful agents for reducing excitotoxic damage (see, e.g., U.S. Pat. No. 4,806,543, Choi 1989). These drugs are discussed in more detail below.

KA and AMPA Antagonists

NMDA receptors are only one of the known classes of EAA receptors. Two other types of EAA receptors are known as:

1. kainic acid (KA) receptors, which are activated by kainic acid; and,

2. QUIS/AMPA receptors, which are activated by quisqualic acid (and its ionized form, quisqualate) and by alpha-amino-3-hydroxy-5-methyl-4-isoxazole (abbreviated as AMPA). Until the mid-to-late 1980's, AMPA receptors were called quisqualate (QUIS) receptors; however, quisqualate also activates a different type of receptor called a metabotropic receptor, so the trend is to call QUIS-type EAA receptors by the name "AMPA" receptors. These receptors are referred to herein as QUIS/AMPA receptors, since both names are still being used in the literature.

KA receptors and QUIS/AMPA receptors are much more closely related to each other than to the NMDA receptor, and they are referred to collectively as non-NMDA receptors. They were not studied nearly as intensively as NMDA receptors during the 1980's, largely because drugs had not been identified which could bind selectively to these receptors and not to NMDA receptors. However, in the late 1980's and early 1990's, major attention began to be paid to KA and QUIS/AMPA receptors, for two reasons: (1) drugs were discovered which can be used as selective probes to analyze binding activity at those receptors, and (2) severe doubt was being cast on the ability of NMDA antagonists to effectively block excitotoxic damage.

Two of the first drugs that were discovered to selectively block activity at KA and QUIS/AMPA receptors were designated as CNQX (6-cyano-7-nitroquinoxaline-2,3-dione) and DNQX (6,7-dinitro-quinoxaline-2,3-dione); see Honore et al 1987 and 1988. Both belong to a class of molecules known as quinoxalinediones. These drugs were used in in vitro (tissue culture) tests, but not in in vivo tests using intact animals since they cannot penetrate the BBB.

Shortly thereafter, an analog known as NBQX (2,3-dihydroxy-6-nitro-7-sulfamoyl-benzo(F)quinoxaline was discovered which penetrates the BBB and which blocks QUIS/AMPA receptors very effectively (Sheardown et al 1989 and 1990). NBQX also blocks KA receptors, but only at somewhat higher concentrations. It shows little or no affinity for NMDA receptors.

More recently, another selective non-NMDA antagonist was discovered which penetrates blood-brain barriers. This compound, 1-(amino-phenyl)-4-methyl-7,8-methylendioxy-5H-2,3-benzodiazepine, has been given the designation GYKI 52466; it is described in Tarnawa et al 1990. GYKI 52466 (referred to herein an GYKI) is a benzodiazepine, with a completely different chemical structure than quinoxalinediones such as NBQX and CNQX. It belongs in the general category of benzodiazepines. The 1,4-benzodiazepines function as tranquilizers by stimulating activity at inhibitory receptors known as gamma-amino-butyric acid (GABA) receptors. GYKI, which is a 2,3-benzodiazepine, apparently has little activation effect on GABA receptors, and instead suppresses ion currents through non-NMDA receptor ion channels. Early data gathered by the Applicant and his coworkers indicate that non-NMDA receptors apparently have a 2,3-benzodiazepine binding site in the receptor complex, and that GYKI binds to that particular binding site as a non-competitive agonist, rather than binding directly to the primary binding site.

NBQX is receiving a great deal of attention due to several reports which stated that it is effective in reducing excitotoxic damage, not just in any tests, but in various in vivo tests in which MK-801 failed to provide effective protection. Reports which describe the benefits of NBQX, when administered by itself in in vivo experiments, include Sheardown et al 1990, Nellgard and Wieloch 1991, and Buchan et al 1991b and 1991c.

The Limitations of MK-801 and NMDA Receptor Blockade

A clear example of the recent research which praises NBQX and describes the failures of MK-801 is set forth in Nellgard and Wieloch 1991, which is entitled, "Postischemic blockade of AMPA but not NMDA receptors mitigates neuronal damage in the rat brain following transient severe cerebral ischemia." This report directly compares NBQX to MK-801 in a model of global ischemia (i.e., ischemia which affects the entire brain, as would occur during cardiac arrest). Nellgard and Wieloch tested both drugs by administering them after the ischemic event; this approximates the treatment that would occur after a patient suffers a stroke.

Similarly, Buchan et al 1991a reported that MK-801 failed to provide effective protection in transient severe forebrain ischemia in rats. Using identical procedures, the same research team then reported that NBQX, by itself, provided effective protection (Buchan et al 1991b). This was followed by yet another report by Buchan et al which stated that NBQX was effective in reducing damage due to focal ischemia (Buchan et al 1991c).

In addition to Buchan et al 1991a, a number of other reports also state that MK-801 is not effective in reducing brain damage in in vivo tests. These reports include:

(1) Michenfelder et al 1989, which involved tests on dogs using a surgical model of complete cerebral ischemia induced by temporary occlusion of the ascending aorta and venae cavae. This report stated, "There was no significant difference in outcome between dizocilpine [MK-801] treated and placebo-treated dogs" (page 228).

(2) Buchan and Pulsinelli 1990, which involved gerbils subjected to temporary surgical occlusion of both carotid arteries, which stated that any protective effect which accompanied MK-801 treatment was due to hypothermia (i.e., reduction of temperature in the brain). MK-801 provided no significant benefit due to direct action at NMDA receptors in animals which were maintained at normal temperatures.

(3) Lanier et al 1990, which involved a period of complete cerebral ischemia in primates (pigtail monkeys). The authors concluded that there was "no significant difference" between the MK-801-treated group and the placebo-treated group. This result was particularly important since it involved primates, which are obviously more directly relevant to humans than tests using rodents or dogs.

In summary, the articles cited above all concur in their conclusion that MK-801 did not provide effective treatment of cerebral ischemia. Therefore, they teach away from the subject invention.

It should also be borne in mind that MK-801 has received so much attention because it would appear to be an ideal agent for blocking NMDA receptors. It is highly specific and selective in its affinity for the PCP-binding site in the NMDA receptor complex, it functions very effectively in shutting down ion currents through the NMDA ion channel, and no other significant molecular interactions are known. Accordingly, articles which report that MK-801 cannot effectively prevent neurotoxicity in certain types of animal tests are necessarily raising major questions about the entire mode of action of MK-801 (i.e., NMDA receptor blockade), rather than merely criticizing the performance of one specific drug. This understanding among neuroscientists is clearly reflected in various statements by neuroscientists, such as the title of the article by Nellgard and Wieloch 1991: "Postischemic blockade of AMPA but not NMDA receptors mitigates neuronal damage . . . " The only NMDA antagonist studied in that article was MK-801, yet Nellgard and Wieloch felt sufficiently confident to broaden their conclusion and state that NMDA blockade, as a mode of action, did not mitigate neuronal damage in the animal model they tested.

Similarly, Pulsinelli and Buchan 1990 offered two rather strong and rather broad conclusions: "We conclude from these data that the NMDA receptor/channel plays little or no role in the pathophysiology of classic selective ischemic necrosis. Furthermore, we conclude that pharmacologic blockade of the NMDA receptor/channel will be of little use in protecting human brain against cardiac arrest" (page 174).

Other Active Disputes Concerning EAA Receptors

The various articles cited above which initially praised MK-801 and then described its failures are merely one example in the ongoing struggle by neuroscientists to clarify and understand the various roles of glutamate and EAA receptors in the brain. Those struggles have often resulted in direct and occasionally severe disputes, wherein claims and assertions by one group of scientists are vigorously or even vehemently denied by other reseachers. Indeed, the history of research on EAA neurotransmitters is an outstanding example of scientists struggling hard and often unsuccessfully to come to grips with apparently contradictory data.

It took an enormous struggle, which lasted for decades, merely for neuroscientists to recognize that glutamate was indeed a neurotransmitter; although the excitatory properties of glutamate and aspartate had been recognized since the 1930's, the most pre-eminent scientists in the field were still adamantly maintaining in the mid-1960's that glutamate had not yet been shown to be a neurotransmitter (Curtis and Watkins 1965). In retrospect, this reluctance is remarkable, since glutamate does not merely play a peripheral role; it is the predominant and most important neurotransmitter in the entire brain.

Subsequently, Olney (the Applicant herein) reported as early as 1969 that orally ingested glutamate caused toxic effects in newborn rodents, and he extended that finding to primates in 1972. Even though those findings could be readily duplicated in any animal research lab, it became a very hotly debated and bitterly contested issue, since food companies and the scientists they funded strongly opposed any efforts to limit the use of monosodium glutamate (MSG, which is the sodium salt of the neurotransmitter) as a flavoring additive in foods (see, e.g., Reynolds et al 1975). Even today, after decades of research, the question of safe levels of MSG in foods has not been resolved.

A number of disputes which directly pertain to the subject invention are also ongoing today. These involve direct disagreements over the question of which EAA receptors must be blocked in order to provide effective protection against excitotoxicity. For example, numerous articles by Choi and his coworkers assert that only NMDA receptors must be blocked; for example, Goldberg et al 1988 states that, "Although glutamate activates both NMDA and non-NMDA receptors (i.e., quisqualate and kainate), blockade of NMDA receptors alone appears to be sufficient to substantially attenuate the ultimate neuronal loss produced either by glutamate or by hypoxia itself" (page 1086). Also see Choi et al 1987, Goldberg et al 1987, Monyer et al 1989, and various other articles for similar quotes. An entirely different research team also reached the same conclusion; as stated in Rothman et al 1991, "the results were quite clear . . . [MK-801] completely blocked the toxicity of glutamate . . . When the specific kainate/quisqualate antagonist CNQX was added, there was little neuronal protection, even though the CNQX was used at 200 uM, a concentration that attenuates glutamate currents by about 90%. These results were consistent with a vital role for NMDA, but not kainate/quisqualate receptors, in glutamate toxicity" (page 104).

These assertions are in stark conflict with the numerous articles which report that MK-801 is not effective in in vivo tests involving adult animals, and with reports such as Sheardown et al 1990 and Nellgard and Wieloch 1991, which state that only non-NMDA receptors must be blocked.

The subject invention sets forth evidence which directly contradicts both of the positions set forth above, i.e., it states and provides powerful evidence, using intact adult animals in an in vivo test that uses actual thrombosis to generate ischemia, that the combination of both drugs is far superior to the protection than can be provided by either agent alone. By contrast, the Choi et al position is based on tissue culture tests using immature neurons, and the Sheardown et al position is based on arbitrary surgical intervention that deviates from the process of thrombosis in several respects.

The differences between the Applicant's assays and the assays used by others are discussed in more detail in the Examples, below. For now, it is worth noting that the findings of the Applicant clearly indicate that both NMDA and non-NMDA receptors must be blocked for optimal protection in at least some situations. Those findings are in direct conflict with the reports of Choi et al and Rothman et al, and with the reports of Sheardown et al and Nellgard and Wieloch, all of which teach away from the subject invention.

The assertion that their teachings, conclusions, and suggestions actively teach away from the subject invention, rather than merely overlooking the Applicant's approach, is confirmed by the fact that none of the cited authors has ever reported testing a combination of both an NMDA antagonist and a non-NMDA antagonist, even though both sides have been engaged in testing both types of agents separately. Even when it would seem to be a simple matter to merely combine two different drugs and test them together, the lines of analysis and experimentation they are following apparently suggest, at least to them, that there is no rationale for combining the two different classes of drugs because the evidence they are seeing suggests that such mixtures would not be helpful.

As yet another example of the current and ongoing conflicts that pertain to this field of science, an abstract (Price et al 1988) which was co-authored by the Applicant was directly contradicted by a full-length article (Zeevalk and Nicklas 1991) which appeared to repeat the exact same experiment and arrive at the opposite results. The abstract and article are analyzed in detail in Examples 1 and 6, below.

This history, although very brief, clearly indicates that there is little or no consensus on the roles of different types of EAA receptors and EAA antagonists in reducing damage due to stroke and other forms of ischemia. Most of the articles cited above teach away from the subject invention, since they assert various competing and often contradictory conclusions that point in different directions from this invention.

Yet another indicator of the conflicts and contradictions that confront neuroscientists trying to reduce ischemic damage by blocking EAA receptors resides in the fact that the Merck drug company, which is widely regarded as one of the best-run companies in the world, invested many years of effort and tens of millions of dollars into its NMDA antagonist MK-801, only to abandon MK-801 in the early 1990's.

Accordingly, even though it is often possible to identify one or more publications which suggest that some particular drug is likely to be effective in reducing neurotoxic damage, the fact is that in this field as a whole, there are few if any answers that rise above the conflicts and contradictions. The single best indicator of the lack of consensus in this field is this: despite the massive medical and social expenses and the personal and family tragedies caused by strokes, not a single drug has been approved by the federal Food and Drug Administration for public use in reducing neurotoxic damage due to stroke.

One object of this invention is to provide a pharmacological agent (a combination of an NMDA antagonist and a non-NMDA antagonist) and method for providing more complete protection against certain types of brain damage than can be achieved by previously described methods.

Another object of this invention is to provide a combination of drugs as described above, with a third drug that functions as a "safener," to protect against the potentially damaging side effects of the NMDA antagonist.

SUMMARY OF THE INVENTION

This invention involves a pharmaceutical mixture for preventing or reducing excitotoxic brain damage caused by hypoxia/ischemia (such as stroke) and various other factors. This mixture comprises an NMDA antagonist and a non-NMDA antagonist, both of which penetrate blood-brain barriers (BBB's) and which, in combination, provide greater protection against excitotoxic damage than can be provided by any quantity of either agent by itself. Suitable NMDA antagonists can be either competitive antagonists which bind directy to the NMDA binding site in the NMDA receptor complex, or non-competitive agents that interact with other binding sites, such as the PCP, glycine, or polyamine binding sites. Suitable non-NMDA antagonists which have been shown to penetrate the BBB in sufficient quantities to provide effective protection for the CNS include a quinoxalinedione compound referred to as NBQX, and a 2,3-benzodiazepine compound referred to as GYKI 52466. This combination of drugs offers much higher levels of protection against excitotoxic neuronal damage than can be obtained by the individual agents acting alone, regardless of quantity.

If an NMDA antagonist is used which is stronger than dextromethorphan, the mixture of an NMDA and a non-NMDA antagonist preferably should be administered in combination with a third agent that functions as a "safening agent" to prevent or reduce the neurotoxic side effects caused by strong NMDA antagonists. Two classes of safening agents have been identified which work by entirely different mechanisms: (1) anti-cholinergic agents, such as scopolamine, atropine, benztropine, trihexyphenidyl, biperiden, procyclidine, benactyzine, or diphenhydramine; and, (2) barbiturates which act as direct agonists of gamma-amino-butyric acid (GABA) receptors, such as secobarbital, pentobarbital, and thiamylal.

DESCRIPTION OF THE PREFERRED EMBODIMENTS

This invention involves a pharmacological mixture and method for protecting against excitotoxic damage to neurons in a mammalian central nervous system. This mixture comprises an NMDA antagonist and a non-NMDA antagonist, both of which penetrate blood-brain barriers (BBB's) to an extent that allows them to inhibit the functioning of excitatory amino acid (EAA) receptors on neurons inside the brain.

One of the key discoveries of the subject invention is that when these two classes of agents are used in combination (such as by mixing them directly together and injecting the mixture into a patient, or by injecting each one into a patient during an overlapping period of time), then the combination can provide a much greater level of neuroprotection than can be achieved by any quantity of either agent by itself. When these agents are administered by themselves, they encounter relatively low "ceiling effects" in their protective action. For example, in the animal model used by the Applicant, which appears to be a highly useful and relevant model for various reasons discussed in the Examples, the drug MK-801 (dizocilpine) by itself cannot provide any level of protection higher than about 40%, regardless of how much of MK-801 is injected into the animal. However, when a combination of an NMDA antagonist and a non-NMDA antagonist are used together, the protection level increases to about 80%, which is far superior to the protection that either agent can provide by itself even in unlimited quantities.

Suitable NMDA antagonists can function through any mechanism which effectively inhibits the flow of ions through the NMDA receptor ion channel. A variety of such agents which can penetrate the BBB and exert protective effects inside the CNS are known. For example, non-competitive NMDA antagonists which activate the phencyclidine receptor include MK-801 (dizocilpine), phencyclidine, ketamine, and tiletamine. Competitive NMDA antagonists that block the NMDA binding site include CGS 19755, CGP 39551, CGP 40116, CGP 37849, CPP, CPP-ene, and NPC 12626. Still other NMDA antagonists act at the polyamine binding site, including ifenprodil and SL 82.0715.

The relevant characteristic of these drugs does not depend on the particular molecular structure of any specific drug; instead, it depends on the ability of an NMDA antagonist to penetrate the BBB and to suppress ion currents through the NMDA ion channel. Accordingly, any of the drugs listed above, and any other NMDA antagonists which are discovered in the future and which have the essential traits (i.e., NMDA antagonist activity inside the BBB) can be routinely screened using in vivo assays such as described in Examples 4 through 6, below, or by using various surgical techniques which generate temporary ischemia by means of clamping arteries for limited periods of time, to determine whether any such NMDA antagonist is more effective in reducing neuronal degeneration when administered in combination with a non-NMDA antagonist, than can be achieved using unlimited quantities of the NMDA antagonist alone.

Two major classes of non-NMDA antagonists which penetrate the BBB and suppress activity at KA and/or QUIS/AMPA receptors have been identified. As described in detail in Examples 3 and 4, each of these drugs has been shown by the Applicant to greatly increase the level of neuroprotection that is provided in an intact adult mammalian model of ischemia, when co-administered with an NMDA antagonist. One of these agents is a quinoxalinedione compound referred to as NBQX (which is 6-nitro-7-sulphamoyl-benzo(f)-quinoxaline-2,3-dione). NBQX is described in articles such as Sheardown et al 1989 and 1990. The other agent is a 2,3-benzodiazepine compound referred to as GYKI 52466 (which is 1-(amino-phenyl)-4-methyl-7,8-methylendioxy-5H-2,3-benzodiazepine). GYKI 52466 is described in Tarnawa et al 1990. As mentioned in the background section, data gathered by the Applicant and his coworkers indicate that non-NMDA receptors apparently have a 2,3-benzodiazepine binding site in the receptor complex, which is distinct from the primary non-NMDA binding site.

With the attention that is being focussed on this area of research, it inevitable that various analogs and derivatives of NBQX and GYKI can and will be developed which will have comparable activity at non-NMDA receptors. Now that these compounds have been identified as having the necessary functional characteristics, any analog of these compounds can be tested for non-NMDA antagonist activity and for BBB penetration, and those analogs that have the two necessary traits can be further screened for superior effectiveness in combination with an NMDA antagonist as described herein.

Safening Agents

Preferably, any NMDA antagonist which is stronger than dextromethorphan, and which is used for the purpose of this invention, should be administered in conjunction with a "safening" agent that reduces or eliminates the neurotoxic side effects that can be caused by strong NMDA antagonists. Such side effects, and two classes of safening agents which can prevent those toxic side effects, are discussed in detail in Examples 8, 9, and 10. These agents include (1) anti-cholinergic drugs such as scopolamine, atropine, benztropine, trihexyphenidyl, biperiden, triperiden, procyclidine, benactyzine, and diphenhydramine, and (2) barbiturates which function as direct agonists at GABA receptors, such as secobarnital, pentobarbital, and thiamylal. Both classes of agents have been tested and shown to prevent vacuole formation in cerebrocortical neurons in lab animals treated with MK-801 or PCP. Therefore, these anti-cholinergic agents can be used as safening agents to prevent the toxic side effects that might otherwise be caused when NMDA antagonists are used to prevent hypoxic/ischemic or other types of brain damage.

The mixtures described herein offer greater protection against excitotoxic brain damage than can be obtained by any agents, mixtures, or methods previously known. The combination of an NMDA antagonist with a non-NMDA antagonist can offer a higher level of protection against hypoxic/ischemic or other excitotoxic brain damage than can be provided by either type of antagonist alone, and the addition of an anti-cholinergic or barbiturate safening agent can prevent or reduce potential side effects caused by the NMDA antagonist.

Included within the compounds of this invention are pharmaceutically acceptable salts of the drugs that are listed herein, as well as pharmaceutically acceptable and therapeutically effective analogs.

Administration of anti-cholinergic compounds to humans can be by any technique capable of introducing the compounds into the bloodstream of a human patient, including intravenous, intramuscular and subcutaneous injections. Some agents are also known to be effective when administered orally. The active compound is usually administered in a pharmaceutical formulation such as in a liquid carrier for injection, or in capsule form for ingestion, although in some acute-care situations an anti-cholinergic agent might be injected without a diluting agent. Such formulations may comprise the active compound (or a mixture of more than one active compounds) together with one or more pharmaceutically acceptable carriers or diluents.

The various components of the mixtures described herein can be mixed together and administered simultaneously (in a single injection, infusion, etc.) if desired. Alternately, they can be administered separately (sequentially, or via different routes of administration), so long as their therapeutic effects overlap in time. In addition, the agents of this invention may be administered in conjunction with one or more thrombolytic agents (i.e., agents which help dissolve blood clots, such as streptokinase or tissue plasminogen activator) if desired.

EXAMPLES

EXAMPLE 1

IN VITRO EMBRYONIC CHICK RETINA ASSAYS

Reif-Lehrer et al 1975 initially described an assay in which pieces of chick retina were isolated and incubated in vitro in various nutrient media. That assay was subsequently modified and adapted by the Applicant and his coworkers in a manner that made it possible to study neuronal degeneration in chick retina induced by various excitotoxin agonists, or by tissue culture conditions that simulate ischemia in some respects. Ischemia (lack of blood supply) was simulated by eliminating the two major constituents of blood (glucose and oxygen) that CNS tissues depend upon for energy. After 30 min of incubation under oxygen/glucose deprived conditions, chick retina tissue displays a neurodegenerative reaction similar to that observed when the retina is incubated in medium containing a toxic concentration of glutamate.

Using that assay, the Applicant and his coworkers conducted a pilot study and reported in a brief abstract (Price et al 1988) that the NMDA antagonist MK-801 or the non-NMDA antagonist CNQX provided little or no protection against simulated ischemia when either agent was used by itself, but that a mixture of MK-801 (500 nanomolar, nM) and CNQX (100 micromolar, uM) could prevent ischemic damage simulated as described above in isolated chick retina tissue.

The above findings were received with skepticism by other scientists working in this field, because the results were at odds with evidence being reported at roughly the same time by several other laboratories using other in vitro simulated ischemia preparations. For example, Choi et al 1987, using cultured neurons from the mouse cerebral cortex, reported that NMDA antagonists protected against simulated ischemic neuronal degeneration with no assistance from non-NMDA antagonists, as described in Example 7, below. Just as importantly, Choi et al also reported that non-NMDA antagonists provided little or no protection for mammalian cells in tissue culture. As quoted above, in the Background section, "Although glutamate activates both NMDA and non-NMDA receptors (i.e., quisqualate and kainate), blockade of NMDA receptors alone appears to be sufficient to substantially attenuate the ultimate neuronal loss produced either by glutamate or by hypoxia itself" (Goldberg et al 1988, page 1086).

Rothman et al 1991 reached the same conclusion, using neurons cultured from another mammalian brain region, the hippocampus. As stated by Rothman et al, "the results were quite clear . . . [MK-801] completely blocked the toxicity of glutamate . . . When the specific kainate/quisqualate antagonist CNQX was added, there was little neuronal protection, even though the CNQX was used at 200 uM, a concentration that attenuates glutamate currents by about 90%. These results were consistent with a vital role for NMDA, but not kainate/quisqualate receptors, in glutamate toxicity" (page 104).

Since both of these researchers obtained favorable results from NMDA antagonists alone, and poor results from non-NMDA antagonists, they did not attempt to evaluate a combination of NMDA and non-NMDA antagonists together. Their findings provided no rationale for conducting such experiments, and indeed teach directly away from the subject invention.

Furthermore, the results published in the Price et al 1988 abstract were directly contradicted by a full-length article which was published recently (Zeevalk and Nicklas 1991). That article, and an explanation of the contradiction, is provided below in Example 7.

Based largely upon the data which were being published during the 1988–1990 time span using mammalian cell assays, it became apparent that the attention and the thrust of research in this field had shifted strongly away from assays involving non-mammalian tissue, and that experimental data which relied on non-mammalian species was not being accepted by the neuroscience community as a reliable indicator or predictor of the behavior of mammalian cells. Accordingly, the Applicant did not pursue his experiments using chick retina tissue beyond the preliminary stages, and did not publish any further evidence pertaining to that simulated model of ischemia. Not only were the chick results in direct conflict with other data being reported by scientists studying mammalian cells using analogous in vitro preparations, but the Applicant also recognized that the chick retina preparation was only a chemically-simulated model of ischemia which uses small pieces of tissue rather than intact organs.

In addition, the chick tissue assay used tissue from embryos or neonates rather than adult animals, and potentially important differences exist between mature and immature neurons. Chick tissue were initially selected for study by Reif-Lehrer et al 1975 and others, because it was hoped that embryonic or neonatal chick tissue would provide a better model of mature neurons than immature mammalian tissue. When chicks hatch, their eyes and retinas are fully formed and functional; they begin looking for food immediately after emerging from an egg. By contrast, baby rodents remain blind with their eyes shut for nearly two weeks after birth, while their retinal tissue continues to mature. Accordingly, since scientists skilled in the art were aware that immature neurons are substantially different from mature neurons in a number of potentially important respects, chick retinal tissue was selected and used during the 1970's and most of the 1980's in an effort to minimize the uncertainties raised by questions of neuronal maturity.

However, by about 1990, it became clear that the focus of most neuroscientists doing in vitro tests had shifted away from non-mammalian tissue and was focusing much more heavily on mammalian tissue. Such assays involving isolated mammalian neurons use immature neurons, since it is exceptionally difficult to induce non-cancerous neurons from adult mammals to replicate in culture. This choice was made despite considerable evidence indicating that immature mammalian neurons contain hypersensitive NMDA receptors and relatively insensitive non-NMDA receptors, as discussed in more detail below.

Since evidence generated using non-mammalian tissue might not be directly applicable to an understanding of mechanisms operative in human neurological disorders such as stroke, and since immature mammalian neurons have different receptor sensitivities than fully mature neurons, the Applicant undertook the development of a more relevant model system using intact adult mammals for studying CNS ischemic neuronal degeneration. This model system is described in Example 2, below.

EXAMPLE 2

PHOTOTHROMBOTIC ISCHEMIA IN INTACT ADULT RATS

A photothrombosis model was developed for studying ischemic neuronal degeneration. It uses a photosensitive dye, rose bengal, which releases singlet oxygen (a highly reactive atom with an unpaired electron) when bright light having a wavelength of 560 nm is shone upon it. If the dye is in the blood stream, the release of singlet oxygen triggers a blood clotting mechanism that causes a clot to form rapidly in the illuminated blood vessel. This method is described in detail in Mosinger and Olney 1989a.

Briefly, adult rats (female Sprague Dawley rats, 200–300 g) were anesthetized with halothane and placed in a stereotaxic holder. Their pupils were dilated with an eye-drop mixture of phenylephrine hydrochloride and tropicamide. A Hamilton microsyringe guided by a micromanipulator was used to inject 7 ul of saline into the vitreous of the right (control) eye, and 7 ul of solution containing CNQX (60 nmol) and/or MK-801 (30 or 160 nmols) into the left (experimental) eye. Plastic contact lenses with a drop of Goniosol were then placed on the corneas of both eyes.

After fifteen minutes, rose bengal dye (40 mg/kg) was injected intravenously through the tail vein. It circulated through the heart and throughout the arterial circulation, including the retina. Both eyes were immediately exposed to 7 min of intense light from slide lantern projectors fitted with a 550 nm filter. The light caused the rose bengal dye in the illuminated blood vessels of the retina to release singlet oxygen, which triggered thrombosis (the formation of blood clots). Within a few minutes the arterial circulation to the retina was totally occluded (blocked by blood clots), leading to ischemia and hypoxia in the retina.

The rats were killed 1 hr later with an overdose of chloral hydrate. The eyes were removed, and the anterior portion (lens, cornea and iris) was excised and discarded. The remaining eyecup was immersed in glutaraldehyde/paraformaldehyde fixative and processed for light microscopy, as described below.

The experimental design (injecting saline into one eye to serve as a control, while injecting CNQX and/or MK-801 into the other eye) allowed one eye of each animal to serve as an internal control for each experiment. If the photothrombosis reaction did not work because the dye was not successfully administered, it would be detected as a photothrombosis failure (no histological damage) in the control eye, and that particular experiment could be voided. In practice, photothrombosis failure rarely occurred; one hour after the occlusion, the control eyes of the test animals quite consistently showed signs of a severe cytopathological reaction which closely resembled the excitotoxic type of reaction that occurs in the retina if a toxic dose of glutamate is injected into the vitreous. This type of reaction, whether caused by photothrombosis or by injection of glutamate into the vitreous, consists of severe swelling of neuronal dendrites and cell bodies with the nuclei of the affected neurons becoming shrunken and dark. These changes occur in three types of retinal neurons referred to as ganglion cell neurons, amacrine neurons, and bipolar neurons. When these neurons show such changes, especially swelling of the cell body and darkening of the nucleus, it is generally considered a sign of irreversible degeneration leading inexorably to cell death. In very early stages of such a reaction, the first pathological change that can be detected is mild swelling of dendrites. If the reaction is arrested at this stage, it is believed that the changes are reversible and the neuron has been saved from cell death.

CNQX is only sparingly soluble in aqueous medium, and the volume of solution that could be injected into the vitreous of the eye without creating abnormal pressure conditions was limited to approximately 7 ul. Therefore, the highest dose of CNQX that could be administered was 60 nanomoles (nmol, which is $10^{-9}$ moles, only ⅟₁₀₀₀th of a micromole). While this dose of CNQX by itself appears to have conferred some protection, the difference in scores between the control and experimental eyes for this group was not statistically significant. Moreover, the range of variation among the experimental eyes treated with CNQX but not MK-801 was considerable, suggesting that any protective effect that may have been operative was highly inconsistent. MK-801 is quite soluble in aqueous medium and it is such a powerful NMDA antagonist that it does not require high doses to block NMDA receptors. In fact, analysis of the data in Table 1 suggests that both of the doses tested (30 and 160 nmol) were high enough to completely block all NMDA receptors. This conclusion follows from the fact that both of the doses tested conferred a similar degree of protection, as would be expected if both blocked the same number of NMDA receptors. The fact that the lower dose provided the same modest degree of protection as the higher dose signifies that this is a ceiling effect constituting the maximum amount of protection that can be obtained by using an NMDA antagonist alone.

To evaluate the neuroprotective effects achieved by the EAA antagonists, light microscopic sections 1 um thick displaying the full extent of each retina were analyzed by two experienced histopathologists. The retinal sections were coded by numbers so the pathologists were not aware of the treatment conditions. The severity of cytopathology was ranked on a scale of zero to +4 based on the degree of dendritic swelling in the inner plexiform layer and the degree of cytoplasmic swelling and nuclear changes in the neurons of the inner nuclear and ganglion cell layers, the specific neural elements of the retina that selectively undergo degeneration under either ischemic conditions or after exposure to a toxic concentration of glutamate. The criteria for scoring were as follows:

Zero=total absence of cytopathology.

+1=very slight cytopathology limited to mild swelling of inner plexiform dendritic processes.

+2=more advanced neuronal degeneration with more conspicuous inner plexiform dendritic swelling plus mild to moderate cytoplasmic and nuclear changes in neurons of the inner nuclear and ganglion cell layers.

+3=the same changes as in a +2 lesion but with 50 to 75% of the affected neurons showing more severe changes, signifying an advanced stage of neuronal degeneration.

+4 =the same changes as in a +3 lesion but with 75–100% of the affected neurons showing very severe changes, signifying uniformly severe cytopathological involvement across the entire retina.

The scores assigned by the two histopathologists for a given retina were usually in perfect agreement but varied in a few cases by a single rating unit. In such cases an average of the two readings was used to determine the final score.

The ratings for the various treatments are presented in Table 1. Differences between the control and experimental eyes were statistically analyzed by the Student's T test. The results indicate that either MK-801 or CNQX by itself provided an equivocal and highly variable amount of protection which could be described as partial at best. The two agents together provided a higher level of protection, with the majority of the retinas being in the 0 or +1 categories.

The adult rat retina photothrombosis model is a highly useful model for studying CNS ischemia, and it is directly relevant to the vast majority of cases of cerebral thrombosis (stroke), for a number of reasons, including the following:

1. The model is based on an actual thrombosis event which generates true and actual ischemia in an intact organ; it does not use chemical manipulations of tissue culture medium, and

TABLE 1

EFFICACIES OF CNQX AND MK-801 IN BLOCKING ISCHEMIC DAMAGE IN IN VIVO ADULT RAT RETINA

| TREATMENT CONDITIONS | | AVERAGE SCORES | | |
|---|---|---|---|---|
| CNQX (nmol) | MK-801 (nmol) | Control (± SEM) | Experimental (± SEM) | n |
| 60 | — | 2.5 (± 0.29) | 1.72 (± 0.43) | 9 |
| — | 160 | 3.1 (± 0.23) | 1.67 (± 0.36) | 9 |
| — | 30 | 3.0 (± 0.28) | 1.59 (± 0.38) | 8 |
| 60 | 160 | 3.4 (± 0.18) | 0.63 (± 0.19) | 12 |
| 60 | 30 | 3.0 (± 0.21) | 0.50 (± 0.17) | 11 | it does not use isolated immature cells in tissue culture.

2. The retina is an actual part of the mammalian CNS. Retinal cells grow directly out from the brain during fetal development, and the retinal cells retain the relevant characteristics of brain tissue, including high concentrations of intracellular glutamate and a high density of the same EAA receptor systems (including both NMDA and non-NMDA receptors) that are found in the adult brain. Extensive evidence suggests that retinal tissue apparently responds to ischemic circumstances in a manner identical to the way neurons in the brain respond.

3. The rose bengal dye test is a relatively simple test which does not require surgical intervention, and it requires only very small quantities of test drugs for each animal. Therefore, large numbers of animals can be tested, and statistically valid results can be compiled with a high level of confidence. This factor is important, since test results for individual animals can be highly variable.

4. Test drugs can be delivered directly to the ischemic tissue, without having to penetrate the blood-brain barrier. The blood-brain barrier, in addition to being an obstacle that many drugs simply cannot overcome, also raises questions concerning experimental drugs that are known to penetrate the BBB to some extent, since it can be difficult to reliably estimate how much of a certain drug has actually reached CNS tissue.

5. The blood-brain barrier issues, and the fact that the photothrombosis model does not require surgery, point toward another advantage of the Applicant's model of photo-induced thrombosis. In a stroke caused by a blood clot becoming lodged in an artery, the flow of blood through the artery is blocked. This raises a major question: how can a drug reach the site of the ischemic CNS tissue, if the blood flow to that region has been stopped? Surgical models of ischemia are widely used because they offer one avenue for overcoming this problem; a set of arteries is clamped and flow through those arteries is shut off for a certain period of time, such as five to fifteen minutes, then the clamps are released and the blood flow is restored. Obviously, this is not an accurate model of what actually happens during a stroke. In human treatment, the use of so-called "clot-buster" drugs such as streptokinase and tissue plasminogen activator offer a highly useful method for dissolving blood clots; however, it is impracticable to test clot-buster drugs in combination with EAA antagonists in animal tests. Accordingly, the model used by the Applicant, which involves actual blood clotting while using an entirely different solution to the problem of allowing the test drugs to reach and interact with the ischemic tissue, is in several respects a better model than artificial surgical interventions.

6. The photothrombosis model can be used to test adult CNS tissue containing mature cells, which have different receptor sensitivities than immature neurons, as discussed in Example 8.

7. It provides a good model of global ischemia in that particular organ. The entire blood supply to the retina is occluded very effectively, in a manner which generates severe ischemic damage if untreated. It therefore offers a challenging model for evaluating protective agents.

For all of these reasons, the rose bengal dye test appears to be well-suited to evaluate whether a drug (or a combination of drugs) can actually protect adult neurons against degeneration during an actual thrombosis event which generates actual rather than simulated ischemia in an intact organ.

Despite those advantages, a crucial shortcoming must be recognized in the experiments described above. CNQX does not penetrate the mammalian BBB. It was used in the Applicant's initial experiments, because no non-NMDA antagonists which could penetrate BBB were available at that time. Therefore, even though CNQX could be used in an experiment involving injection into the interior of an eye, using a protocol that was specifically designed to circumvent the BBB problem, the CNQX tests did not teach or suggest a practical treatment for stroke victims.

EXAMPLE 3

IN VIVO ASSAYS OF MK-801 COMBINED WITH NBOX

In 1989 and 1990, Sheardown et al reported that (1) a non-NMDA antagonist known as NBQX had been identified which can penetrate the mammalian BBB, and (2) NBQX, by itself and without co-administration of an NMDA antagonist, could reduce excitotoxic damage in intact adult mammals, using in vivo tests.

Despite the teachings of Sheardown et al that NBQX could reduce neurodegeneration by itself, and despite the apparent lack of interest in such combinations among other research teams, the Applicant decided to test NBQX in combination with MK-801, using the rose bengal dye model described in Example 2. These tests were performed using the same procedures and evaluation criteria described in Example 2, using photo-induced thrombosis to generate ischemic conditions in the retina. In each animal, one eye (which was injected with saline) served as the control, while the other eye (injected with MK-801 and/or NBQX) was the experimental eye. All injections were of 7 microliters and were made into the vitreous humor of the eye.

In these experiments, MK-801 was tested at 30 nmole per eye. In previous experiments, MK-801 had been tested by itself over a wide range of dosages (ranging from 3 to 160 nmoles) and it was found that MK-801 quickly reaches a "ceiling level" of protection; any dose in excess of 10 nmoles provided approximately 25–40% protection, with considerable variability from one experiment to another, regardless of dose. The 40% protection level was the maximum amount of protection obtainable with MK-801 by itself, and increasing the dose beyond 10 nmoles did not provide any additional protection. Nevertheless, the Applicant tripled the 10 nmole dosage and administered 30 nmoles, in order to give MK-801 every opportunity to provide as much protection as possible.

The NBQX (a gift from Dr. Tage Honore of Novo Nordisk, in Denmark) was tested at only one dose (60 nmoles) because it is subject to solubility limitations as described above for CNQX.

The data were gathered using the scale of damage ranging from 0 for no detectable damage to +4 for extreme damage, as described above. Mean values were calculated for all similarly treated eyes, and the mean values for treated and untreated (saline control) eyes were compared.

The results indicated that NBQX, when administered by itself to 8 rats, reduced the level of damage by about 30%, while MK-801, when administered by itself to 16 rats, reduced the level of damage by 40%.

By contrast, when NBQX was administered in combination with MK-801, damage was reduced by 82%

These results clearly indicate that when an NMDA antagonist which penetrates the blood brain barrier is administered in conjunction with a non-NMDA antagonist which also penetrates the blood-brain barrier, the combination reduces neurotoxic ischemic damage in CNS neurons by a much greater degree than either drug acting alone can provide, even in unlimited quantities. The NMDA antagonist MK-801 was tested across a wide dosage range and was shown to be subject to a ceiling effect when used by itself; a maximal amount of protection (40% or less) was all that could be obtained, regardless of quantity. Similarly, in a separate set of tests, NBQX was used at a dose which was as high as solubility limitations permitted, yet it was not able, by itself, to provide more than about 30% protection against ischemic damage. Despite those celinig limitations on both of the component drugs, the Applicant demonstrated that the damage level was reduced to only about 20% of the controls when the two drugs were combined. The 80% protection level is vastly superior to the protection that either type of agent could accomplish by itself.

EXAMPLE 4

IN VIVO ASSAYS OF MK-801 COMBINED WITH GYKI 52466

In 1990, in a publication that appeared after the filing of parent application Ser. No. 467,139, Tarnawa et al reported the discovery that a drug designated as GYKI 52466 (referred to herein as GYKI; the full chemical name is 1-(amino-phenyl)-4-methyl-7,8-methylendioxy-5H-2,3-benzodiazepine) penetrates the BBB and selectively inhibits activity at non-NMDA receptors, primarily QUIS/AMPA receptors. This was shown in tests which involved the inhibition of spinal cord reflexes in cats; these tests did not involve ischemia, and Tarnawa et al did not teach or suggest that GYKI 52466 could be combined with other drugs such as NMDA antagonists for treatment of ischemia.

GYKI has an entirely different structure than quinoxalinediones such as CNQX and NBQX. It belongs in the general category of benzodiazepines, which are primarily of interest as tranquilizers because 1,4-benzodiazepines stimulate activity at inhibitory receptors known as gamma-aminobutyric acid (GABA) receptors. By contrast, GYKI is a 2,3-benzodiazepine which apparently has little or no effect at GABA receptors.

The Applicant tested a sample of GYKI (a gift from Dr. Istvan Tarnawa of the Institute for Drug Research in Budapest, Hungary) in the in vivo photothrombosis assay described in Examples 2 and 3, with and without co-administration of MK-801. Because of solubility limitations when aqueous buffer was used, the maximum dosage of GYKI that could be administered without injecting excessive quantities of fluid into the vitreous of the eye was 100 nmoles.

The tests indicated that GYKI 52466, administered by itself to 6 rats, reduced neuronal damage by 25%. As noted above, MK-801, reduced the level of damage by 40% when administered at 30 nmol per eye.

However, when a combination of GYKI and MK-801 was administered, damage was reduced by 71%. This level of protection was much greater than either component could achieve by itself.

In subsequent tests, the Applicant has administered substantially higher quantities of GYKI (up to 500 nm), by dissolving it in dimethyl sulfoxide (DMSO) rather than aqueous solution. When administered at higher quantities, the maximal level of protection afforded by GYKI is in the range of about 40%, using the above criteria.

When the maximal effective dosage of GYKI is combined with a relatively low quantity of MK-801 which provides only about 15% protection, the combination provides a protection level of about 80%. Again, this is far superior to any protection level that can be provided by either component drug by itself.

EXAMPLE 5

IN VIVO ASSAY USING A BROAD SPECTRUM EAA ANTAGONIST

It has been shown in several in vitro preparations that kynurenate, or its structural analog, 7-chlorokynurenate, have broad spectrum blocking action against the neurotoxic action of both NMDA and non-NMDA agonists, with the potency against NMDA agonists being approximately three times greater than against non-NMDA agonists. Based on the results from the experiments described above, in which it was shown that blocking both NMDA and non-NMDA receptors provided better protection against ischemic damage than blocking only one or the other receptor type, the Applicant reasoned that a broad spectrum EAA antagonist might provide a high degree of protection against ischemic damage.

Using the in vivo photothrombosis model described above, kynurenate or 7-chlorokynurenate were tested for their ability to protect against ischemic neuronal degeneration. Intravitreal injection of kynurenate or 7-Cl-kynurenate provided partial protection at low doses (wherein the activity presumably was limited to blocking NMDA receptors) and greater than 90% protection at higher doses (both NMDA and non-NMDA receptors blocked).

Neither kynurenate nor 7-Cl-kynurenate can penetrate blood brain barriers. Therefore, these agents do not offer a useful therapeutic agent for preventing CNS damage due to stroke or other forms of ischemia. However, the kynurenate and 7-Cl-kynurenate results in the photothrombosis assay, in which drugs that have been injected directly into the vitreous do not need to penetrate the BBB to reach the retinal neurons, clearly and directly corroborate and support the Applicant's demonstration that in vivo blockade of both NMDA and non-NMDA receptors in an adult mammal provides optimal protection, whereas only partial protection is achieved by blocking only NMDA receptors or only non-NMDA receptors.

A further implication of these findings is that it does not matter whether a broad-spectrum blockade of NMDA and non-NMDA receptors is achieved by a single agent or a combination of agents. In adult mammals, superior protection is achieved regardless of what particular drug or combination of drugs is used (provided that activity at both NMDA and non-NMDA receptors is inhibited), compared to the degree of protection that can be obtained by blocking only one or the other class of receptor.

EXAMPLE 6

CHICK RETINA STUDIES REVISITED

As mentioned above, in Example 1, the Applicant abandoned his in vitro chick retina studies after obtaining findings that were incongruous with in vitro evidence that was being published by numerous other laboratories. However, in light of his subsequent observation that the in vitro chick retina findings tended to correlate well with the results of the in vivo adult rat retina photothrombosis model of CNS ischemia, the Applicant decided to undertake a new series of experiments to ascertain the basis for the disparity between his in vitro findings and the results published by other researchers.

In particular, the Applicant wanted to determine the reason for a directly contradictory report, Zeevalk and Nicklas 1991, which used an apparently identical model, the chick embryo retina. The Applicant and his coworkers had obtained relatively low levels of protection against simulated ischemic damage, using either an NMDA or non-NMDA antagonist by itself, as reported in the Price et al 1988 abstract. In direct contrast to both findings, Zeevalk and Nicklas 1991 reported that an NMDA antagonist by itself protected very effectively, and a non-NMDA antagonist conferred no protection at all.

Based on those results, Zeevalk and Nicklas did not even test a combination of the two agents, even though they had all necessary reagents and it would have been a simple matter to simply mix them together.

Since the findings of Zeevalk and Nicklas were in full agreement with those reported earlier by Choi et al using cerebrocortical cell cultures and by Rothman et al using hippocampal cell cultures, the Zeevalk and Nicklas report was accepted in this field of science as the reasonable and apparently reliable result. Accordingly, the Applicant's earlier chick retina findings, which had already been dismissed by most of the Applicant's peers, were considered to be directly refuted.

The Applicant became very curious to find out why the results from the different labs were directly opposed, so he undertook a detailed and careful analysis of the experimental protocol of Zeevalk and Nicklas. This analysis revealed a significant difference between their protocol and the Applicant's protocol, as follows: Zeevalk and Nicklas used a high concentration (25 mM) of a certain buffer component known as MOPS (the abbreviation for 3-(N-morpholino) propanesulfonic acid) in their incubation medium. In contrast, the Applicant, in his prior experiments which were described in the Price et al abstract, had used MOPS at a concentration of only 5 mM.

Therefore, the Applicant undertook experiments to determine whether the MOPS concentration is an important variable that could explain the disparate results. These experiments were conducted using various concentrations of MOPS (5, 10, 15, 20 and 25 mM) and studying whether these concentrations affected the acute toxicity of agonists that exert excitotoxic activity at either NMDA or non-NMDA receptors. These agonists included kainic acid, quisqualate, and AMPA, which activate non-NMDA receptors.

It was found that the two higher concentrations of MOPS tested by the Applicant (20 and 25 mM) exerted a strong blocking action against excitotoxicity mediated by all three of the above-listed non-NMDA agonists; however, MOPS did not significantly reduce the toxicity exerted by the agonist NMDA.

Thus, in the experiments by Zeevalk and Nicklas, although they reported that they obtained excellent blocking action with an NMDA antagonist alone and could not obtain blocking action with a non-NMDA antagonist, the excellent protection observed was actually due to the fact that they were unknowingly blocking both NMDA and non-NMDA receptors; NMDA receptors being blocked by the NMDA antagonist they were testing, and the non-NMDA receptors were being blocked by the high concentration of MOPS in their buffer solution. In their tissue preparation, the non-NMDA receptors were already being blocked by MOPS in the buffer; therefore, glutamate, being unable to act at the non-NMDA receptors, was causing neuronal degeneration exclusively by action at NMDA receptors. It follows that the use of an NMDA antagonist in a high-MOPS buffer would indeed provide excellent protection, and little or no effect would be seen from addition of a non-NMDA antagonist drug, because the non-NMDA receptors were already blocked by the MOPS.

This result, although it apparently was not recognized by Zeevalk and Nicklas when they did their experiment or published their report, actually provides additional confirmation and support for the Applicant's finding that a combination of drugs (or a single broad-spectrum EAA antagonist) which can block both NMDA and non-NMDA receptors can provide the best protection against excitotoxic damage due to ischemia.

The question arises whether MOPS could be considered a useful agent for protecting against ischemic neuronal degeneration. The answer is, it appears to be highly unlikely, because in order for an agent to be of pharmaceutical interest, it must exert blocking action at concentrations low enough to be free from serious side effects. The NMDA and non-NMDA antagonists that are being evaluated by neurologists are all effective in low micromolar ranges. By contrast, it required 20 to 25 mM MOPS to exert a neuroprotective effect, and the millimolar range is a thousand times more concentrated than the micromolar ranges used for MK-801, NBQX, and GYKI 52466.

EXAMPLE 7

DEXTROMETHORPHAN TESTS

Dextromethorphan and dextrorphan are two nonaddictive morphine enantiomers which are widely used in cough syrup, and which activate several inhibitory receptors while also inhibiting activity at NMDA receptors. Due to their activity as NMDA antagonists, dextromethorphan and dextrorphan have been claimed by Choi et al to be useful for anti-ischemic therapy (U.S. Pat. No. 4,806,543, and Choi et al 1987). The assertions by Choi et al are based on experiments using cerebrocortical cell cultures, involving mammalian cells which are isolated while in the immature (fetal or neonatal) stage. Dextromethorphan, by itself, provided good protection against simulated ischemia in that particular model, so the Applicant evaluated DM in the chick retina model. In that model, DM failed to block ischemic damage. However, when combined with a non-NMDA antagonist (either NBQX or GYKI), the combination gave very high levels of protection.

The ability of DM by itself to protect against ischemic neuronal degeneration in the particular model used by Choi et al may be due to the fact that Choi's preparation consists of highly immature (fetal or neonatal) cultured mammalian cells. An intrinsic feature of immature cultured mammalian neurons is that they possess hypersensitive NMDA receptors and insensitive non-NMDA receptors. This is confirmed by various reports which indicate that immature cells are easily damaged by low concentrations of NMDA, while they are not easily damaged even by substantially larger concentrations of non-NMDA antagonists such as kainic acid, quisqualate, and AMPA. In addition, high concentrations of non-NMDA antagonists are needed to provide any degree of protection against glutamate-induced or ischemic damage in immature mammalian neurons. By contrast, as mentioned above, the chick retina, although immature, is a significantly more mature system; the newborn chick can already see to hunt for food. All EAA receptor types in the chick retina behave as mature receptor systems, which respond to toxic circumstances in a manner that is directly comparable to adult receptors. Thus, both NMDA and non-NMDA receptors in the chick retina, as in the adult brain, participate in mediating ischemic neuronal degeneration, and both systems must be blocked to prevent ischemic damage.

All of the foregoing results clearly indicate that an NMDA antagonist which penetrates the blood brain barrier, if administered in conjunction with a non-NMDA antagonist which also penetrates the blood-brain barrier, can reduce neurotoxic ischemic damage in mature CNS neurons by a much greater level than either type of antagonist acting alone. These two classes of compounds, when used in combination, have been shown to provide a higher degree of protection against actual ischemia in an intact adult mammal than any other pharmacological agent or mixture previously reported.

EXAMPLE 8

USE OF ANTI-CHOLINERGIC DRUGS AS SAFENING AGENTS

The above-cited parent application Ser. No. 424,548, which issued as U.S. Pat. No. 5,034,400, disclosed that a class of drugs known as anti-cholinergic drugs (since they suppress activity at cholinergic receptors) can be used as "safening" agents to prevent or reduce the toxic side effects caused by NMDA antagonists. Those toxic side effects include vacuole formation and mitochondrial damage in neurons of the cingulate cerebral cortex. Those toxic side effects, and the anti-cholinergic drugs which can be used to prevent or reduce them, are described in more detail in U.S. Pat. No. 5,034,400, the contents of which are hereby incorporated by reference. Additional pertinent references are Olney et al 1989, and Olney et al 1991.

One of the teachings of the subject invention is that when a combination of:

(1) an NMDA antagonist:

(2) a non-NMDA antagonist; and, (3) a safening agent is used to prevent excitotoxicity, that triple-combination provides highly effective protection, due to two effects: (1) the NMDA and non-NMDA antagonists provide a higher level of primary protection than can be achieved by either agent acting alone; and, (2) the anti-cholinergic agent provides a secondary level of protection, to minimize any side effects that might otherwise be caused by the NMDA antagonist.

This teaching is further supported by the following example.

EXAMPLE 9

POTENTIAL SIDE EFFECTS ASSOCIATED WITH DRUG COMBINATIONS

The question whether a combination of NMDA and non-NMDA antagonists will cause life-threatening side effects (such as failure of the lungs or heart) was also tested by the Applicant. MK-801 was injected subcutaneously at a dosage of 1 mg per kilogram of body weight; this is the dose widely used by others to show neuroprotection in brain ischemia models). The MK-801 was administered in combination with GYKI 52466, which was injected subcutaneously at 30 mg/kg (the upper limit of the dose range used by others to protect against seizures).

This combination was tolerated by adult rats without any observable interference in vital functions such as respiration or heart beat. However, the pathomorphological changes typically caused by NMDA antagonists (described in Olney et al 1989) were conspicuously evident in neurons of the cingulate cerebral cortex.

Adding the anti-cholinergic drug scopolamine (0.25 mg/kg subcutaneously) as a safening agent prevented the cerebrocortical neurotoxic side effects of MK-801. The triple combination (MK-801, GYKI, and scopolamine) was tolerated without any observed interference in vital functions (n=6 rats per treatment group).

When an NMDA antagonist and non-NMDA antagonist combination, or a broad-spectrum EAA antagonist which blocks both NMDA and non-NMDA receptors, are administered together with a safening agent such as an anti-cholinergic or barbiturate drug which prevents the neurotoxic side effects of the NMDA antagonist, the three-component mixture is believed to be the safest and most effective pharmacological treatment ever discovered for reducing or preventing severe neurotoxic damage in the central nervous system due to hypoxia or ischemia.

EXAMPLE 10

USE OF BARBITURATES AS SAFENING AGENTS

Another co-pending patent application which was invented by the same Applicant (Ser. No. 734,210, filed on Jul. 22, 1991) discloses that certain types of barbiturates (particularly certain thiobarbiturates) can also serve as safening agents to prevent or reduce the toxic side effects caused by NMDA antagonists. The contents of that application are hereby incorporated by reference, and that application will be opened for public inspection upon the issuance of a U.S. patent based on the instant application. Additional pertinent information is provided in Olney et al 1991.

Briefly, in order to exert a high level of effectiveness for use as a safening agent as described herein, a barbiturate must be able to act as a "direct" agonist at GABA receptors. This means that they must be able to directly activate GABA receptors, even in the absence of GABA. By contrast, "indirect" GABA agonists such as benzodiazepines can potentiate the activity of GABA at GABA receptors, but they cannot open GABA-controlled channels in the absence of GABA. Barbiturates which function as direct GABA agonists include secobarbital and pentobarbital, as well as thiobarbiturates such as thiamylal.

The subject invention discloses that barbiturates can be used as safening agents in triple-component mixtures that also contain an NMDA antagonist and a non-NMDA antagonist. This is directly comparable to the use of anti-cholinergic drugs as safening agents, as described in Examples 8 and 9, with one exception: at least some types of barbiturates inhibit the functioning of internal organs that interact directly with nerve signals from the brain, including the heart and lungs. Accordingly, a barbiturate should be used as a safening agent as described herein only if a patient is being constantly monitored, such as in an intensive care unit. Typically, such patients are maintained on respirators during the period of barbiturate administration.

Thus, there has been disclosed a class of pharmacological agents which can function safely and effectively in accomplishing beneficial results that were not previously available. This invention therefore satisfies all of the objectives set forth herein. Although this invention has been described with respect to specific embodiments, the details of these embodiments are not to be construed as limitations. Various equivalents and modifications may be made without departing from the spirit and scope of this invention, which is limited only by the claims that follow.

REFERENCES

Ascher, P., et al, *Glutamate, Cell Death and Memory* (Springer-Verlag, New York, 1991)

Boast, C. A., "Neuroprotection after brain ischemia: role of competitive NMDA antagonists," *Neurology and Neurobiology* 46: 691–698 (1988)

Buchan, A. and Pulsinelli, W. A., "Hypothermia but not the NMDA antagonist MK-801 attenuates neuronal damage . . . ," *J. Neuroscience* 10: 311–316 (1990)

Buchan, A. M., "Do NMDA antagonists protect against cerebral ischemia: Are clinical trials warranted?" *Cerebrovasc. and Brain Metab. Rev.* 2: 1–26 (1990)

Buchan, A. M., et al, "Blockade of the AMPA receptor prevents CA1 hippocampal injury following severe but transient forebrain ischemia in adult rats," *Neurosci. Letters* 132: 255–258 (1991)

Choi, D. W., et al, "Dextrorphan and levorphanol selectively block NMDA receptor-mediated neurotoxicity on cortical neurons," *J Pharmacol Exp Ther* 242(2): 713–720 (1987)

Drejer, J., et al., "A new potent glycine antagonist FG 9067 (MNQX) shows anti-convulsant activities," *J. Neurochem.* 52: Suppl., S42-D (1989).

Goldberg, M. P., et al, "NMDA receptors mediate hypoxic neuronal injury in cortical culture," *J Pharmacol Exp Ther* 243(2): 784–791 (1987)

Goldberg, M. P., et al, "Phencyclidine receptor ligands attenuate cortical neuronal injury after NMDA exposure or hypoxia," *J Pharmacol Exp Ther* 245(2): 1081–1086 (1988)

Honore, T., et al, "Potent and competitive antagonism at non-NMDA receptors by FG 9041 and FG 9065," *Soc. Neurosci. Abstr.* 13: 383 (1987)

Honore, T., et al, "Quinoxalinediones: potent competitive non-NMDA glutamate receptor antagonists," *Science* 241: 701–703 (1988)

Honore, T., et al, "Quisqualate receptor specific quinoxalinedione (FG 9202, NBQX) blocks kainate induced responses," *J. Neurochem.* 52: Suppl., S42-A (1989)

Kemp, J. D., et al, "Non-competitive antagonists of excitatory amino acid receptors," *Trends in Neurosci.* 10: 294 (1987)

Krause, G. S., et al, "Brain cell death following ischemia and reperfusion: A proposed biochemical sequence," *Critical Care Medicine* 16: 714–726 (1988)

Krieglstein, J., *Pharmacoloay of Cerebral Ischemia* 1989 (Wissenschaftliche Verlagsgesellschaft, Stuttgart, Germany, 1989)

Krieglstein, J., and Oberpichler, H., *Pharmacology of Cerebral Ischemia* 1990 (Wissenschaftliche Verlagsgesellschaft, Stuttgart, Germany, 1990)

Lanier, W., et al, "The effects of dizocilpine . . . in primates," *Anesthes. Rev.* 15: 36–37 (1988)

Lubec and Rosenthal (eds.), *Amino Acids: Chemistry. Biology. and Medicine* (ESCOM Science Publishers, Leiden, Netherlands, 1990)

Meyer, F. B., et al, "Focal Cerebral Ischemia: Pathophysiological Mechanisms and Rationale for Future Avenues of Treatment," *Mayo Clin. Proc.* 62: 35–55 (1987)

Michenfelder, J., et al, "Evaluation of the glutamate antagonist dizocilpine . . . ," *Brain Research* 481: 228–234 (1989)

Monyer, H., et al, "Glucose deprivation neuronal injury in cortical culture," *Brain Res* 483: 347–354 (1989)

Mosinger, J. L. and Olney, J. W., "Photothrombosis-Induced Ischemic Neuronal Degeneration in the Rat Retina," *Exp. Neurol.* 105: 110–113 (1989)

Nellgard, B. and Wieloch, T., "Postischemic blockage of AMPA but not NMDA receptors mitigates neuronal damage in the rat brain following transient severe cerebral ischemia," *J Cereb Blood Flow Metab* 12: 2–11 (1992)

Nellgard, B., et al, "Lack of protection by the NMDA receptor blocker dizocilpine (MK-801) after transient severe cerebral ischemia in the rat," *Anesthesiology* 75: 279–287 (1991)

Olney, J. W., et al, "Pathological changes induced in cerebrocortical neurons by phencyclidine and related drugs," *Science* 244: 1360–1362 (1989)

Olney, J. W., et al, "NMDA antagonist neurotoxicity: Mechanism and Prevention," *Science* 254: 1515–1518 (1991)

Price, M. T., et al, "CNQX potently and selectively blocks kainate excitotoxicity in the chick embryo retina," *Soc. Neurosci. Abstr.* 14: 418 (1988)

Pulsinelli, W. A. and Buchan, A., "The NMDA receptor/ion channel: Its importance to in vivo ischemic injury to selectively vulnerable neurons," pp. 169–174 in Krieglstein and Oberpichler 1990.

Reif-Lehrer et al, "Effects of monosodium glutamate on chick embryo retina in culture," *Invest. Ophthalmol.* 14: 114–124 (1975)

Reynolds, W. A., et al, "Hypothalamic morphology following ingestion of aspartame or MSG in the neonatal rodent and primate: A preliminary report," *J Toxicol Environ Health* 2: 471 (1976)

Rothman, S. M., and Olney, J. W., "Glutamate and the Pathophysiology of Hypoxia-Ischemic Brain Damage," *Annals of Neurology* 19(2): 105–111 (1986)

Rothman, S. M., et al, "In vitro neuronal death: Contrasts between excitotoxicity and chemical hypoxia," in

*Glutamate, Cell Death and Memory* (P Ascher, et al, eds., Springer-Verlag, Berlin Heidelberg, 1991)

Sheardown, M. J., et al, "NBQX, a specific non-NMDA receptor antagonist, shows neuroprotective effects against cerebral ischemia," abstract published in *Proceedings of the First International Conference on Therapy with Amino Acids and Analogs*, Vienna, Aug. 7–12, 1989.

Sheardown, M. J., et al, "Blockade of AMPA receptors in the CA1 region of the hippocampus prevents ischaemia induced cell death," pp. 245–253 in Krieglstein and Oberpichler 1990.

Tarnawa, I., et al, "GYKI 52466, an inhibitor of spinal reflexes, is a potent quisqualate antagonist," pp. 538–546 in Lubec and Rosenthal 1990

Watkins, J. C., "Excitatory Amino Acids," in *Kainic Acid as a Tool in Neurobiology* (E. G. McGeer et al, eds., Raven Press, New York, 1978)

Wauquier, A., et al, "Cerebral resuscitation: Pathophysiology and therapy," *Neurosci. Biobehav. Rev.* 11: 287–306 (1987)

Wong, E. H. F., et al, "The Anticonvulsant MK-801 Is A Potent N-Methyl-D-Aspartate Antagonist," *Proc. Nat'l. Acad. Sci U.S.A.* 83: 7104–7108 (September 1986)

Zeevalk, G. D. and Nicklas, W. J., "Chemically induced hypoglycemia and anoxia: Relationship to glutamate receptor-mediated toxicity in retina," *J Pharmacol Exp Ther* 253(3): 1285–1292 (1990)

I claim:

1. In the method of using an NMDA antagonist to reduce excitotoxic damage in a mammal suffering such damage, the improvement consisting of co-administering, along with a therapeutically beneficial quantity of an NMDA antagonist which penetrates blood-brain barriers, a therapeutically effective quantity of a non-NMDA antagonist which also penetrates blood-brain barriers, wherein the quantities of the NMDA antagonist and the non-NMDA antagonist in combination provide a greater level of protection against excitotoxic damage than can be achieved by any quantity of either agent administered alone.

2. The method as recited in claim 1, wherein the excitotoxic damage is occurring as a result of ischemia.

3. The method as recited in claim 1, wherein the excitotoxic damage is occurring as a result of hypoxia.

4. The method of claim 1, wherein the NMDA antagonist acts by a mechanism which involves activation of the phencyclidine receptor.

5. The method of claim 4, wherein the NMDA antagonist is selected from the group consisting of (+)-5-methyl-10,11-dihydro-5H-dibenzo[a,d]cyclohepten-5,10-imine maleate (common name MK-801), phencyclidine, ketamine, and tiletamine.

6. The method of claim 1, wherein the NMDA antagonist is a competitive NMDA antagonist that occupies NMDA binding sites in NMDA receptor complexes.

7. The method of claim 6, wherein the NMDA antagonist is selected from the group consisting of:

cis-4-phosphonomethyl-2-piperidinecarboxylic acid (common name CGS 19755);

D,L(E)-2-amino-4-methyl-5-phosphono-3-pentenoic acid carboxyethyl ester (common name CGP 39551);

2-amino-4-methyl-5-phosphono-3-pentenoic acid (common name CGP 37849);

4-(3-phosphonopropyl)-2-piperazine-carboxylic acid (common name CPP);

(e)-4-(3-phosphonoprop-2-enyl)piperazine-2-carboxylic acid (common name CPP-ene);

D-(E)-2-amino-4-methyl-5-phosphone-3-pentenoic acid) (common name CGP 40116); and, 2-amino-4,5-(1,2-cyclohexyl)-7-phosphonoheptanoic acid (common name NPC 12626).

8. The method of claim 1, wherein the NMDA antagonist blocks a glycine receptor or a polyamine receptor that functions as a part of an NMDA receptor complex.

9. The method of claim 8 wherein the NMDA antagonist is selected from the group consisting of 4-benzyl-alpha-(p-hydroxyphenyl)-beta-methyl-1-piperidine-ethanol (common name ifenprodil); (+)-2-(4-chlorophenyl)-4-[(4-fluorophenyl)methyl]-1-piperidineethanol (common name SL 82.0715); and 5,7-dinitroquinoxaline-2,3-dione (common name MNQX).

10. The method of claim 1, wherein the non-NMDA antagonist comprises a quinoxalinedione compound.

11. The method of claim 10, wherein the quinoxalinedione compound comprises 6-nitro-7-sulphamoyl-benzo(f) quinoxaline-2,3-dione (common name NBQX).

12. The method of claim 1, wherein the non-NMDA antagonist comprises a benzodiazepine compound which suppresses ion currents through non-NMDA receptor channels.

13. The method of claim 12, wherein the benzodiazepine compound comprises 1-(amino-phenyl)-4-methyl-7,8-methylendioxy-5H-2,3-benzodiazepine (common name GYKI 52466).

14. A method for reducing hypoxic or ischemic damage to neurons in a mammalian central nervous system, comprising the administration of therapeutically effective dosages of:

a. an NMDA antagonist which penetrates blood-brain barriers in quantities sufficient to inhibit the functioning of NMDA receptors; and, b. a non-NMDA antagonist which penetrates blood-brain barriers in quantities sufficient to inhibit the functioning of at least one type of non-NMDA receptor, wherein the NMDA antagonist and the non-NMDA antagonist, in combination, provide a greater level of protection against excitotoxic damage than can be achieved by any quantity of either agent administered alone.

15. The method of claim 14, wherein the non-NMDA antagonist comprises a quinoxalinedione compound selected from the group consisting of 6-nitro-7-sulphamoylbenzo(f)-quinoxaline-2,3-dione (common name NBOX), and pharmaceutically acceptable, therapeutically effective salts and analogs thereof.

16. The method of claim 14, wherein the non-NMDA antagonist comprises a 2,3-benzodiazepine compound selected from the group consisting of 1-(amino-phenyl)-4-methyl-7,8-methylendioxy-5H-2,3-benzodiazepine (common name GYKI 52466), and pharmaceutically acceptable, therapeutically effective salts and analogs thereof.

17. A pharmaceutical composition, comprising a mixture of an NMDA antagonist and a non-NMDA antagonist, wherein both antagonists penetrate blood-brain barriers in quantities sufficient to inhibit the functioning of excitatory amino acid receptors, and wherein the NMDA antagonist and the non-NMDA antagonist, in combination, provide a greater level of protection against excitotoxic damage than can be achieved by any quantity of either agent administered alone, and wherein the the NMDA antagonist is selected from the group consisting of (+)-5-methyl-10,11-dihydro-5H-dibenzo[a,d]-cyclohepten-5,10-imine maleate (common name MK-801); phencyclidine; ketamine; tiletamine; cis-4-phosphonomethyl-2- piperidinecarboxylic acid (common name CGS 19755); D,L(E)-2-amino-4-methyl-5-phosphono-3-pentenoic acid carboxyethyl ester (common name CGP 39551); 2-amino-4-methyl-5-phosphono-3-pentenoic acid (common name CGP 37849); 4-(3-phosphonopropyl)-2-piperazine-carboxylic acid (common name CPP); (e)-4-(3-phosphonoprop-2-enyl)piperazine-2-carboxylic acid (common name CPP-ene); D-(E)-2-amino-4-methyl-5-phosphone-3-pentenoic acid) (common name CGP 40116); and 2-amino-4 5-(1,2-cyclohexyl)-7-phosphonoheptanoic acid (common name NPC 12626), and pharmaceutically acceptable, therapeutically effective salts and analogs thereof;

and wherein the non-NMDA antagonist is selected from the group consisting of 6-nitro-7-sulphamoyl-benzo(f) quinoxaline-2,3-dione (common name NBOX) and 1-(amino-phenyl)-4-methyl-7,8-methylendioxy-5H-2, 3-benzodiazepine (common name GYKI 52466), and pharmaceutically acceptable, therapeutically effective salts and analogs thereof.

* * * * *